United States Patent
Kasin et al.

(10) Patent No.: US 10,146,993 B2
(45) Date of Patent: Dec. 4, 2018

(54) NON-INVASIVE MULTIMODAL BIOMETRICAL IDENTIFICATION SYSTEM OF ANIMALS

(71) Applicant: ADVANCED APPLIED TECHNOLOGIES LTD., Hong Kong (CN)

(72) Inventors: Kjell Ivar Kasin, Notodden (NO); Clas Gerhard Sivertsen, Taipei (TW)

(73) Assignee: ADVANCED APPLIED TECHNOLOGIES LTD., Hong Kong (CN)

(*) Notice: Subject to any disclaimer, the term of this patent is extended or adjusted under 35 U.S.C. 154(b) by 96 days.

(21) Appl. No.: 15/312,696

(22) PCT Filed: May 19, 2015

(86) PCT No.: PCT/CN2015/079252
§ 371 (c)(1),
(2) Date: Nov. 21, 2016

(87) PCT Pub. No.: WO2015/176637
PCT Pub. Date: Nov. 26, 2015

(65) Prior Publication Data
US 2017/0103257 A1    Apr. 13, 2017

Related U.S. Application Data

(60) Provisional application No. 62/000,890, filed on May 20, 2014.

(51) Int. Cl.
G06K 9/00 (2006.01)
A01K 29/00 (2006.01)
(Continued)

(52) U.S. Cl.
CPC .......... *G06K 9/00362* (2013.01); *A01K 29/00* (2013.01); *A01K 29/005* (2013.01);
(Continued)

(58) Field of Classification Search
CPC .......... G06K 9/00006; G06K 9/00073; G06K 9/00093; G06K 9/00362;
(Continued)

(56) References Cited

U.S. PATENT DOCUMENTS 8,190,544 B2    5/2012  Angell et al.
2004/0153477 A1  8/2004  Meadows
(Continued)

FOREIGN PATENT DOCUMENTS

CN    1598866 A    3/2005
CN  101453947 A    6/2009
(Continued)

*Primary Examiner* — Andrew W Johns
(74) *Attorney, Agent, or Firm* — Locke Lord LLP; Tim Tingkang Xia, Esq.

(57) ABSTRACT

A non-invasive biometrical identification method and system (100) of animals, comprising: receiving characteristic data of an individual from at least one biometric sensor (102); processing the characteristic data to form biometric data identifying minutiae based skin markings of the individual and biometric data identifying physical characteristics of the individual; evaluating the biometric data identifying minutiae based skin markings of the individual and biometric data identifying physical characteristics of the individual to form biometric characteristic data of the individual; comparing the biometric characteristic findings of the individual to characteristic data of predetermined registered individuals; determining whether the individual is registered; giving the individual a unique identification if the individual is not registered; and registering the unique identification in a data storage (112).

17 Claims, 6 Drawing Sheets

(51) Int. Cl.
*A01K 61/90* (2017.01)
*A01K 61/95* (2017.01)
*A01K 45/00* (2006.01)
*A61B 5/1171* (2016.01)
*A61B 5/00* (2006.01)

(52) U.S. Cl.
CPC .............. *A01K 45/00* (2013.01); *A01K 61/90* (2017.01); *A01K 61/95* (2017.01); *A61B 5/1171* (2016.02); *G06K 9/00335* (2013.01); *G06K 9/00885* (2013.01); *G06K 9/00892* (2013.01); *A61B 5/444* (2013.01); *A61B 2503/40* (2013.01)

(58) Field of Classification Search
CPC ..... G06K 2009/00395; G06K 9/00885; G06K 9/00892
See application file for complete search history.

(56) References Cited

U.S. PATENT DOCUMENTS

| | | | |
|---|---|---|---|
| 2004/0208343 A1 | 10/2004 | Golden et al. | |
| 2008/0140234 A1 | 6/2008 | Shafter | |
| 2009/0208064 A1* | 8/2009 | Cambier | 382/110 |
| 2012/0275663 A1* | 11/2012 | Craft et al. | 382/115 |
| 2013/0142398 A1 | 6/2013 | Polimeno et al. | |

FOREIGN PATENT DOCUMENTS

| | | |
|---|---|---|
| CN | 103164773 A | 6/2013 |
| EP | 0821912 A2 | 2/1998 |
| EP | 1018297 A1 | 7/2000 |
| TW | 201400811 A | 1/2014 |
| WO | 2007/077694 A1 | 7/2007 |
| WO | 2007/103886 A2 | 9/2007 |
| WO | 2011/143711 A1 | 11/2011 |

\* cited by examiner

NON-INVASIVE MULTIMODAL BIOMETRICAL IDENTIFICATION SYSTEM OF ANIMALS

BACKGROUND OF THE INVENTION

Field of the Invention

The present invention generally relates to a method, a system, one or more computational units, and a computer program product for non-invasive biometrical identification of animals, particularly a method, a system, and a computer program product using minutiae based skin markings in combination with physical characteristics for non-invasive biometrical identification of animals.

Description of the Prior Art

Farm animal identification is a major requirement for government agricultural authorities, facilitating registration of animals, recording of authorized animal movements, herd management, and payments of appropriate grants and subsidies and as a vital tool in tracing diseases of public and animal health concern. Furthermore, farmers and integrated food suppliers even retailers have requirements for specific traceability of their animal products to identify growth characteristics on an individual basis as well as identification of the food animal origins for history of feed and feed ingredients, disease and treatment details.

Most identification schemes are based on a computer database of ear-tag numbers. A potential limitation of such systems has been their tracking of a device attached to the animal, rather than tracing the animal itself. This becomes problematic when accidental loss or fraudulent switching of tags occurs, as preserving correct identification is difficult.

The more manual oriented based identification systems are generally invasive in the sense that herd separation is required for the individual to be read, analyzed and registered. It involves active participation of specialists, veterinary services and even extensive participation of mechanical machinery, equipment and boats in the case of aquaculture. The costs to enable the reading are high. Furthermore, the obvious drawback is that its data are historical, confirming the fact as they are not used continuously due to their invasive character. That is why the data collected from the traditional systems are of limited use and not specific enough to be an active tool to proactively offset actions upon abnormalities in data reading.

For aquaculture in particular, and the Atlantic salmon (*Salmo salar*) industry in Norway and Chile besides UK, Ireland, Faroe Islands, US, Canada, and Tasmania, as a good example, this is very obvious. The aquaculture of Atlantic salmon is an unprecedented success starting back in the early 1970ies in Norway. In 2014 the total production from the markets referred above was more than 2 million metric tons, or more than 500 million individual fish. To mark or tag each fish individually is practically impossible.

An increasing problem is escapees of cultured fish from cages that are invading and spawn with local wild species thus are polluting the local gene pool. The legislation against escapees is serious in for example Norway, with relatively high penalties for the aquaculture farmer if he can be identified to be the source of the escapees. One idea that has gained traction is to DNA identify each fish or family of fish and then conduct DNA testing of suspected escapees that are found in the rivers. The disadvantage with this method besides being costly is that the DNA testing takes too long time thus cannot proactively be used to identify other escapees, thus weed out from the waterway.

Other methods of identification are fin clipping, retina ink, and transponder insertion; however, all require a lot of handling and are expensive and also negative as far as animal welfare goes. Accordingly, a non-invasive identification and real-time monitoring system for animals is needed.

SUMMARY OF THE INVENTION

In a first aspect, the present invention provides a computer implemented method for non-invasive biometrical and morphometric data identification of animals. The computer implemented method comprises:

receiving characteristic data of an individual from at least one biometric sensor;

processing the characteristic data to form data identifying minutiae based skin markings of the individual and biometric data identifying physical characteristics of the individual;

evaluating the biometric data identifying minutiae based skin markings of the individual and biometric data identifying physical characteristics of the individual to form biometric characteristic data of the individual;

comparing the biometric characteristic data of the individual to characteristic data of predetermined registered individuals;

determining whether the individual is registered;

giving the individual a unique identification if the individual is not registered; and registering the unique identification in a data storage.

The computer implemented method of the present invention may further comprise:

linking the unique identification of the individual to a behavior data collecting system from at least one collecting behavior sensor.

In some embodiments, the at least one biometric sensor comprises at least one of gyro stabilized 2D cameras and gyro stabilized 3D cameras. In some embodiments, the at least one biometric sensor further comprises a laser device on the at least one of gyro stabilized 2D cameras and gyro stabilized 3D cameras to lock on to a target.

In some embodiments the camera may comprise an auto-focusing apparatus that allows sharp pictures to be taken at various focusing lengths. In other embodiments the camera may comprise a fixed focus lens that may capture blurry images for objects that does not fall within the fixed focus distance. In such embodiments the computer implemented method may contain algorithms to discard images that are not in focus.

In some embodiments, the animals are fish, and the physical characteristics of the individual comprise at least one of body shape, eye, snout, mouth, gilds and fin location, and melanophore constellations. In some embodiments, the animals are birds, the identifying minutiae based skin markings of the individual comprise minutiae based feather markings, and the physical characteristics of the individual comprise at least one of body shape, eye, beacon, wing and leg location. In some embodiments, the animals are pigs, and the physical characteristics of the individual comprise at least one of body shape, eye, snout, mouth, ear, leg and tail location.

The computer implemented method of the present invention may further comprise at least one of the following steps:

processing and discarding images that are not in focus, have visual defects, artifacts, or that are otherwise not suitable for further processing;

processing and analyzing by looking at numbers of individuals within an specific area or volume;

processing and analyzing by looking for un-normal behavior or sick individuals;

processing and analyzing by looking for growth rates or volume of individuals increase or decrease;

processing and analyzing animal health;

processing and analyzing pandemic control;

processing and analyzing animal health and using the processed and analyzed data for pandemic control; and processing and re-rendering the characteristic data to be able to manually view the data, connected to a unique identification of an individual, and for a person to inspect findings as an image or film.

In a second aspect, the present invention provides a system for non-invasive biometrical identification of animals. The system comprises:

at least one biometric sensor, and the at least one biometric sensor captures characteristic data of an individual;

a characteristic data processing engine, and the characteristic data processing engine processes the characteristic data of the individual to form biometric data identifying minutiae based skin markings of the individual and biometric data identifying physical characteristics of the individual;

a biometric data evaluating engine, and the biometric data evaluating engine evaluates the biometric data identifying minutiae based skin markings of the individual and biometric data identifying physical characteristics of the individual to form biometric characteristic data of the individual; and a biometric characteristic data comparing engine, and the biometric characteristic data comparing engine compares the biometric characteristic data of the individual to characteristic data of predetermined registered individuals, determines whether the individual is registered, gives the individual a unique identification if the individual is not registered, and registers the unique identification in a data storage.

In some embodiments, the at least one biometric sensor comprises at least one of gyro stabilized 2D cameras and gyro stabilized 3D cameras. In some embodiments, the at least one biometric sensor further comprises a laser device on the at least one of gyro stabilized 2D cameras and gyro stabilized 3D cameras to lock on to a target. In some embodiments, the at least one biometric sensor comprises at least one camera equipped with an autofocusing apparatus that allows sharp pictures to be taken at various focusing lengths. In other embodiments, the at least one biometric sensor comprises at least one camera equipped with a fixed focus lens that capture blurry images for objects that does not fall within the fixed focus distance.

In some embodiments, the animals are fish, and the physical characteristics of the individual comprise at least one of body shape, eye, snout, mouth, gilds and fin location. In some embodiments, the animals are birds, the identifying minutiae based skin markings of the individual comprise minutiae based feather markings, and the physical characteristics of the individual comprise at least one of body shape, eye, beacon, wing and leg location. In some embodiments, the animals are pigs, and the physical characteristics of the individual comprise at least one of body shape, eye, snout, mouth, ear, leg and tail location.

In some embodiments, the at least one biometric sensor captures behavior data of the individual.

In some embodiments, the characteristic data processing engine comprises algorithms to discard images that are not in focus.

The system of the present invention may further comprise:

a behavior data comparing engine, and the physiological characteristic data comparing engine compares physiological characteristic data with a predetermined range of acceptable values for the physiological characteristic data;

at least one parameter characteristic sensor, and the at least one parameter characteristic sensor captures a parameter characteristic of a condition; and a parameter characteristic processing engine, and the parameter characteristic processing engine receives the parameter characteristic of a condition with a predetermined range of acceptable values and transmits a signal if the individual is registered, if the physiological characteristic data is within the predetermined range, and if the parameter characteristic of the condition to be within the range of acceptable values for the parameter.

Furthermore, the system of the present invention may further comprise a data processing and analyzing engine. The data processing and analyzing engine processes and analyzes at least one of: numbers of individuals within an specific area or volume, un-normal behavior or sick individuals, growth rates or volume of individuals increase or decrease, animal health, and pandemic control, or processes and re-renders the characteristic data to be able to manually view the data, connected to a unique identification of an individual, and for a person to inspect findings as an image or film.

In a third aspect, the present invention provides a computer program product for non-invasive biometrical identification of animals. The computer program product comprises:

a non-transitory computer recordable-type medium;

first program instructions for receiving characteristic data of an individual from at least one biometric sensor;

second program instructions for processing the characteristic data to form biometric data identifying minutiae based skin markings of the individual and biometric data identifying physical characteristics of the individual;

third program instructions for evaluating the biometric data identifying minutiae based skin markings of the individual and biometric data identifying physical characteristics of the individual to form biometric characteristic data of the individual;

fourth program instructions for comparing the biometric characteristic data of the individual to characteristic data of predetermined registered individuals, determining whether the individual is registered, giving the individual a unique identification if the individual is not registered, and registering the unique identification in a data storage; and the first program instructions, the second program instructions, the third program instructions, and the fourth program instructions are stored on the non-transitory computer recordable-type medium.

The computer program product of present invention may further comprise:

fifth program instructions for linking the unique identification of the individual to receive behavior data of the individual from the at least one biometric sensor;

sixth program instructions for comparing behavior" data with a predetermined range of acceptable values for the physiological characteristic data;

seventh program instructions for receiving a parameter characteristic of a condition with a predetermined range of acceptable values for the parameter transmitting a signal if the individual is registered, if the physiological characteristic data is within the predetermined range, and if the parameter characteristic of the condition to be within the range of acceptable values for the parameter; and the fifth program instructions, the sixth program instructions, and the seventh program instructions are stored on the non-transitory computer recordable-type medium.

Furthermore, the computer program product of present invention may further comprise eighth program instructions for processing and analyzing at least one of: numbers of individuals within an specific area or volume, un-normal behavior or sick individuals, growth rates or volume of individuals increase or decrease, animal health, and pandemic control, or processing and re-rendering the characteristic data to be able to manually view the data, connected to a unique identification of an individual, and for a person to inspect findings as an image or film, wherein the eighth program instructions are stored on the non-transitory computer recordable-type medium.

BRIEF DESCRIPTION OF THE DRAWINGS

FIG. 5(*b*) is an example of identifying a salmon with 9 minutiae based skin markings (such as b1, b2, and b3) when the salmon is small, and FIG. 5(*c*) is the same example of identifying the same salmon with the 9 minutiae based skin markings (such as b1', b2', and b3') when the salmon grows bigger.

FIG. 5(*d*) is an example of identifying a salmon with markings of the end point of lower jaw (d1), the front point of pectoral fin (d2), the front point of dorsal fin (d3), and the central point of an eye (d4) when the salmon is small, and FIG. 5(*e*) is the same example of identifying the same salmon with the markings of the end point of lower jaw (d1'), the front point of pectoral fin (d2'), the front point of dorsal fin (d3'), and the central point of an eye (d4') when the salmon grows bigger.

DETAILED DESCRIPTION OF THE PREFERRED EMBODIMENT

Figure 1:
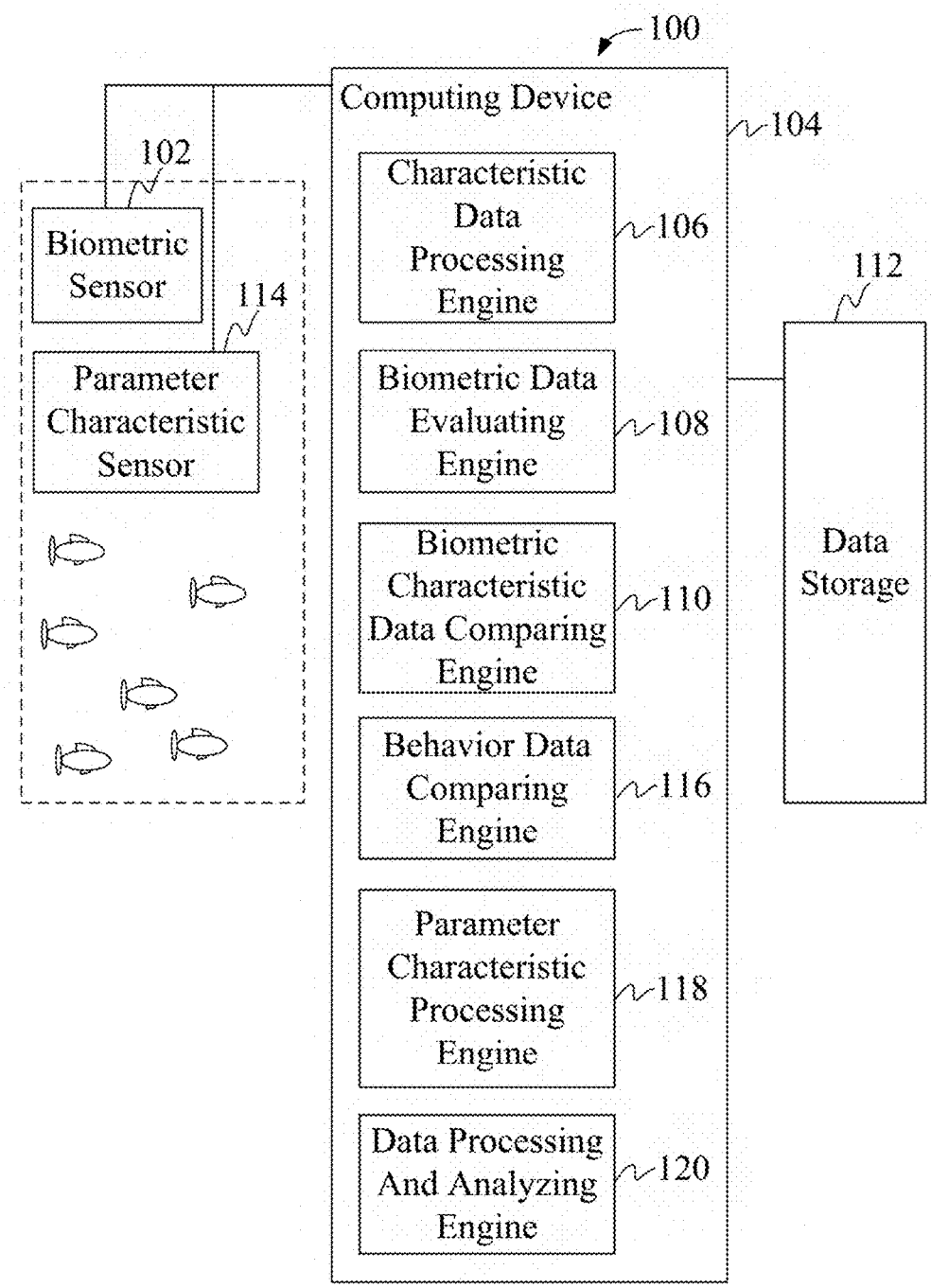
FIG. 1 is a block diagram of a system for non-invasive biometrical identification of animals in accordance with an illustrative embodiment.

The present invention provides a real time method of collecting morphometric characteristics from an individual fish using minutiae based skin markings in combination with physical characteristic like body shape, eye, snout, mouth, gilds and fin location without using eye component like iris or retina.

The present invention also provides a real time method of collecting morphometric characteristics from an individual bird using minutiae based skin and feather markings in combination with physical characteristic like body shape, eye, beacon, wing and leg location without using eye component like iris or retina.

The present invention further provides a real time method of collecting morphometric characteristics from an individual pig using minutiae based skin markings in combination with physical characteristic like body shape, eye, snout, mouth, ear, leg and tail location without using eye component like iris or retina.

The present invention also provides a real time method of collecting morphometric characteristics from an none human individual using minutiae based skin markings in combination with physical characteristic like body shape, eye, snout, mouth, ear, leg and tail location without using eye component like iris or retina.

As stated above, in order to sense biometric characteristic data of the individual, the present invention uses a laser device to locate the area of the biometric characteristics and measure the biometrical findings on the individual.

As stated above, the sensor collects the pre-processing data within the sensor itself.

As stated above, the sensor organizes collected behavior and characteristic data of the individual.

As stated in above, the sensor sends the data to a computer to be further processed, filtered and analyzed.

As stated above, the computer compares the biometric characteristic data to characteristic data of predetermined registered individuals, determines whether the individual is registered, compares the physiological characteristic data with a predetermined range of acceptable values for said physiological characteristic data, and senses a parameter characteristic of a condition with a predetermined range of acceptable values for the parameter transmitting a signal if the individual is registered, if the physiological characteristic data is within the predetermined range or not, and if the parameter characteristic of the conditions to be within the range of acceptable values for the parameter.

As stated above, the computer uses the analyzed biometric characteristic data to give the individual a unique ID.

As stated above, the computer links the unique ID of the individual to the captured behavior-data of that individual.

As stated above, the computer sends the processed data to a central data storage in the purpose of further processing and analyzing, looking at numbers of individuals within an specific area or volume.

As stated above, the computer sends the processed data to a central data storage in the purpose of further processing and analyzing, looking for un-normal behavior or sick individuals.

As stated above, the computer sends the processed data to central data storage in the purpose of further processing and analyzing, looking for growth rates or volume increase or decrease.

As stated above, the computer sends the processed data to a central data storage in the purpose of further processing and analyzing animal health and or pandemic control.

As stated above, the computer sends the processed data to a central data storage in the purpose of further processing and analyzing animal health and/or use the data for pandemic control.

As stated above, the computer sends the processed data to a central data storage in the purpose of further processing and re-rendering the vector based images to be able to manually view the collected data, connected to an individual ID, and for a person to inspect the findings as an image or film.

FIG. 1 is a block diagram of a system for non-invasive biometrical identification of animals in accordance with an illustrative embodiment. The system 100 has a biometric sensor 102, a characteristic data processing engine 106, a biometric data evaluating engine 108, a biometric characteristic data comparing engine 110, a data storage 112, a parameter characteristic sensor 114, a behavior data comparing engine 116, a parameter characteristic processing engine 118, and a data processing and analyzing engine 120. The characteristic data processing engine 106, the biometric data evaluating engine 108, the biometric characteristic data comparing engine 110, the behavior data comparing engine 116, the parameter characteristic processing engine 118, and the data processing and analyzing engine 120 are provided in software installed on a computer 104. The computer 104 is connected to the biometric sensor 102 and the parameter characteristic sensor 114. The computer 104 is also connected to the database 112, which stores data for biometrical identification of animals.

The biometric sensor 102 captures characteristic data and behavior data of an individual. The characteristic data are images of an individual. The biometric sensor 102 is at least one gyro stabilized 2D cameras and/or at least one gyro stabilized 3D cameras equipped with a laser device to lock on to a target. Optionally, the biometric sensor 102 is at least one camera equipped with an autofocusing apparatus that allows sharp pictures to be taken at various focusing lengths or at least one camera equipped with a fixed focus lens that may capture blurry images for objects that does not fall within the fixed focus distance.

The characteristic data processing engine 106 processes the characteristic data of the individual to form biometric data identifying minutiae based skin markings of the individual and biometric data identifying physical characteristics of the individual. In addition, the characteristic data processing engine 106 has algorithms to discard images that are not in focus.

When the individual is a fish, the physical characteristics of the individual include, but not limited to, at least one of body shape, eye, snout, mouth, gilds and fin location. When the individual is a bird, the identifying minutiae based skin markings of the individual include minutiae based feather markings, and the physical characteristics of the individual include, but not limited to, at least one of body shape, eye, beacon, wing and leg location. When the individual is a pig, the physical characteristics of the individual include, but not limited to, at least one of body shape, eye, snout, mouth, ear, leg and tail location.

The biometric data evaluating engine 108 evaluates the biometric data identifying minutiae based skin markings of the individual and biometric data identifying physical characteristics of the individual to form biometric characteristic data of the individual.

The biometric characteristic data comparing engine 110 compares the biometric characteristic data of the individual to characteristic data of predetermined registered individuals, determines whether the individual is registered, gives the individual a unique identification if the individual is not registered, and registers the unique identification in the data storage 112.

The behavior data comparing engine 116 compares behavior data with a predetermined range of acceptable values for the behavior. The parameter characteristic sensor 114 captures parameter characteristics of a condition. The parameter characteristics include but not limited to altitude, temperature, humidity, salinity, illumination, pressure, noise, cuts, scratches, bites, contamination on the sensor, translation directions: up, down, left, right, rotation: roll and yaw.

The parameter characteristic processing engine 118 receives the parameter characteristic of a condition with a predetermined range of acceptable values and transmits a signal if the individual is registered, if the physiological characteristic data is within the predetermined range, and if the parameter characteristic of the condition to be within the range of acceptable values for the parameter.

The data processing and analyzing engine 120 processes and analyzes at least one of: numbers of individuals within an specific area or volume, un-normal behavior or sick individuals, growth rates or volume of individuals increase or decrease, animal health, and pandemic control, or processes and re-renders the characteristic data to be able to manually view the data, connected to a unique identification of an individual, and for a person to inspect findings as an image or film.

Figure 2:
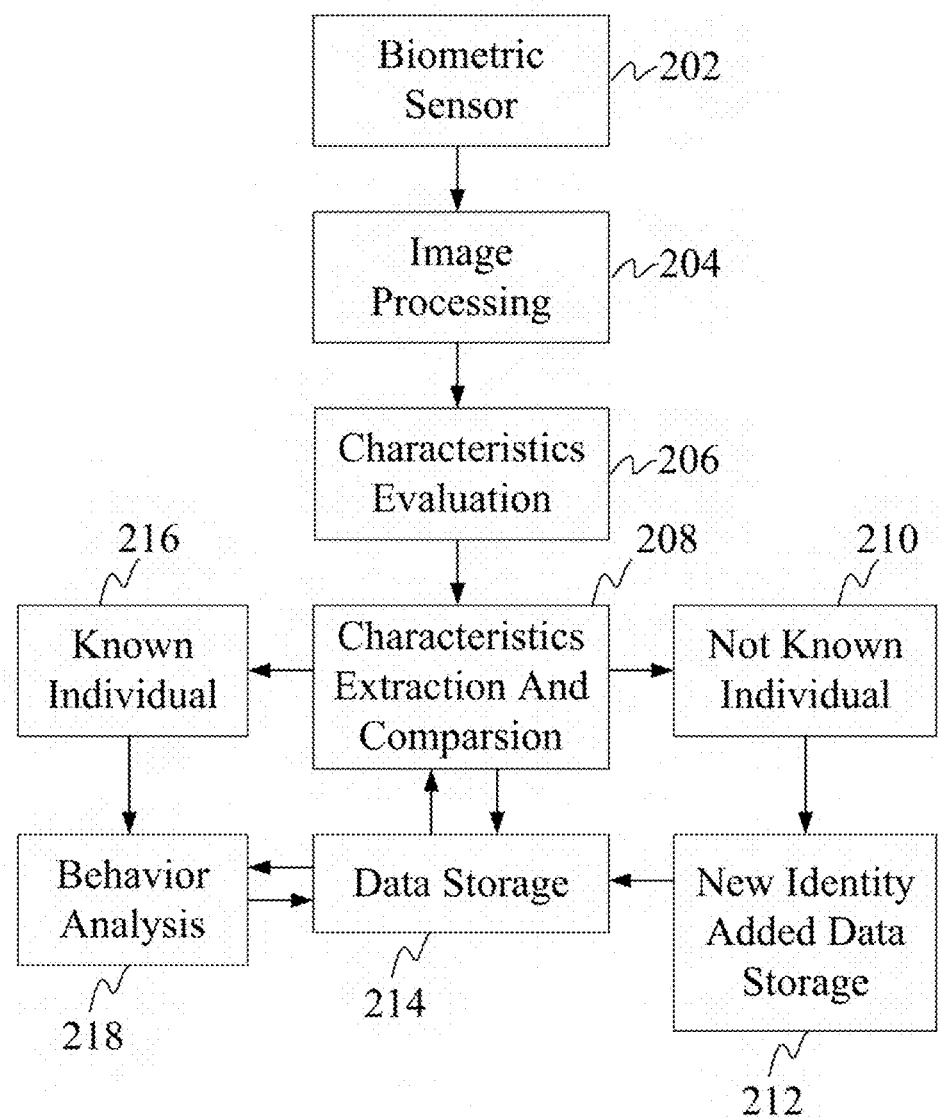
FIG. 2 is a process flow diagram of a method for non-invasive biometrical identification of animals in accordance with an illustrative embodiment

FIG. 2 depicts a process flow diagram of a method for non-invasive biometrical identification of animals in accordance with an illustrative embodiment. Characteristic data of an individual, such as images of the individual, are captured by at least one biometric sensor 202 and processed 204 to form biometric data identifying minutiae based skin markings of the individual and biometric data identifying physical characteristics of the individual. The biometric data identifying minutiae based skin markings of the individual and the biometric data identifying physical characteristics of the individual are evaluated 206 to form biometric characteristic data of the individual. The biometric characteristic data of the individual are extracted and compared 208 to characteristic data of predetermined registered individuals to determine whether the individual is registered. If the individual is not registered 210, a unique identification 212 is given to the individual and registered in a data storage 214. If the individual has been known and registered 216, the unique identification of the individual is linked to receive behavior data of the individual from the biometric sensor, the behavior data are analyzed 218, and the analyzed data are stored in the data storage 214.

Figure 3:
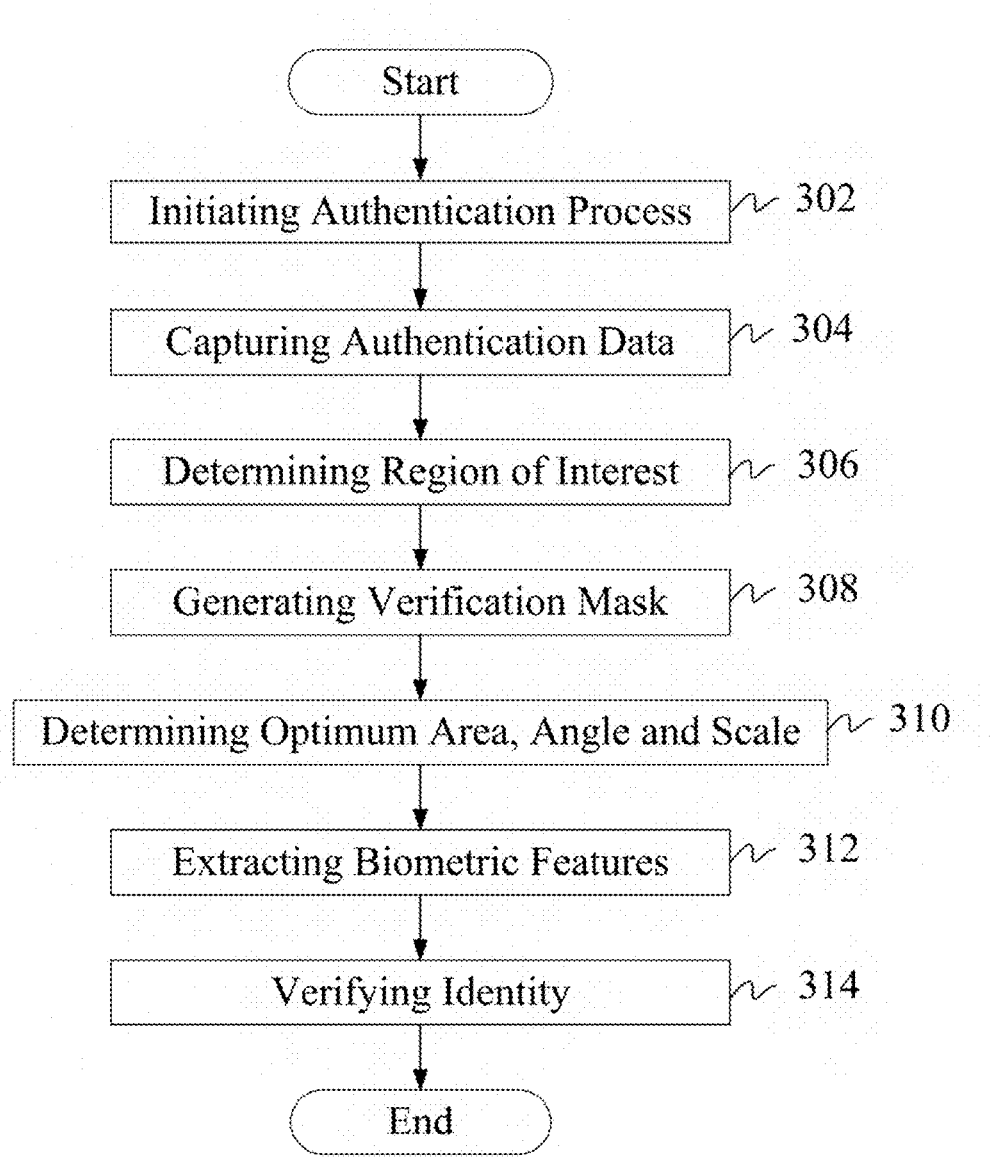
FIG. 3 is a flowchart of a process for verifying identities in accordance with an illustrative embodiment.

FIG. 3 is a flowchart of a process for verifying identities in accordance with an illustrative embodiment. The process depicted in FIG. 3 may be implemented in software, such as characteristic data processing engine 106, biometric data evaluating engine 108, and biometric characteristic data comparing engine 110 in FIG. 1.

The process begins by initiating an authentication process 302, and then capturing authentication data 304 to determine which regions are region of interest to be analyzed 306. After that, verification mask is generated 308 to determine which areas, angles, and scales of the authentication data are going to be optimized 310. Then, biometric features are extracted from the optimized data 312, and finally identity of an individual is verified 314.

Further explanation of the present invention by using fish as an example is provided as follows.

Multi-Biometrics

Multimodal systems are those that combine more than one biometric identifier. A biometric system, which relies only on a single biometric identifier, is often not able to meet the desired performance requirements. By using minutiae based skin markings together with unique mouth shape, eye location, fin shape and gill location, the present invention is able to seek out a unique individual fish and give it an unique identity and next identify it among other fishes.

Data Collecting Sensor

One or more sensors or are used to collect the data and convert the information to a digital format. Signal processing algorithms perform quality control activities and develop the biometric template. A data storage component keeps information that new biometric templates will be compared to. A matching algorithm compares the new biometric template to one or more templates kept in data storage. Finally, a decision process uses the results from the matching component to make a system-level decision.

If the pattern formation of a fish can be described by the same model or process as for all other individuals of this species, the question arises, why all patterns are different except for the structure type. The reason is that the final fine pattern strongly depends on the initial conditions and the boundary conditions. The initial condition may be a random pattern, in which even small changes may force large variations in the final pattern, if the model is nonlinear. A boundary condition may be an external environmental condition (e.g., temperature, pressure, light condition, salinity etc.) or the shape of the individual.

Biometric Sensor

To be able to collect biometric data from swimming fish, high-resolution 2D and 3D, gyro-stabilized cameras with a zoom function in combination with a motion detecting system that has the ability to lock on to an object/target (individual fish) are needed. By using integrated compact underwater lasers for scaling, references and measuring, additional data are able to be added to the system.

Fish or Not

Algorithms that analyze a potential moving target (as a moving fish), is implemented, by recognizing the shape and vectors of an object identified as an acceptable object (as a fish) to be tracked. An example of locating shape and vectors using snout and tail on a fish is to use Haar-like features in a boosted classifier setup. The results of independent detection of the snout and tail using Haar detectors has been further improved using relationships between the detected snouts and tails, for instance by constraining the search for tail detection based on the results of snout detection and vice versa. A heuristic threshold is used to eliminate noise and reduce non-fish edges on the basis that higher magnitudes indicated stronger edges.

Tracking

If the analyzing software accepts the criteria of the object (fish) to be in a position that generates an acceptable biometrical data, collection the data will be by taking high-resolution pictures of the object (fish). The data will, in real-time, be further processed filtered and converted to vector based pictures. If the computer demands a tracking sequence to be able to collect data, the fish is tracked using a motion detection algorithm, as an example, using a combination of two algorithms:

A feature vector based on centroid of the image area, the motion vector, the area of the fish and the orientation (angle of the principal axis), comparing changes from frame to frame against heuristic thresholds.

Color matching in HSV (hue, saturation, value) space using a comparison of pixel values against the probability that the hue belongs to the histogram of the target object.

By adding data from compact underwater lasers for scaling, reference and other measurings together with data from high-resolution cameras (video cameras), the biometric data quality can be secured.

Image Processing

Using a wide dynamic range, lens distortion correction, noise reduction, colors correction and defective pixel correction the image enhancement and a powerful computer does the vectorizing. For example, methods of image processing have been described by Patterson et al. ("Constructing and Rendering Vectorised Photographic Images," Journal of Virtual Reality and Broadcasting, volume 9(2012), no. 3; urn:nbn:de:0009-6-32713) and in U.S. Pat. Nos. 6,735,695, 7,421,097, 7,769,207, 7,991,199, 8,190,544, 8,355,543, 8,442,279, and 8,879,804. The methods of image processing are incorporated herein by reference.

Characteristics Extraction

With biometrics, rather than compare the entire image, biometric points are placed at key locations and measurements between all the points are taken. Using multimodal systems more than one biometric is combined to increase the ability to identify an individual.

The results are compiled into a "score." Such a score can be easily obtained from every image and stored in the database. When a new individual's image is obtained, all that is required for a successful identification, of that individual, is the system to compile the "score" based on the image's biometrics and compare this new score to the scores in the database.

In other words, a biometric system does the verification or authentication of the individual by analyzing the score with other stored scores of individuals. The system confirms or denies the identity of the individual. The challenge is to collect a high quality score from an individual in its habitat.

Figure 4:
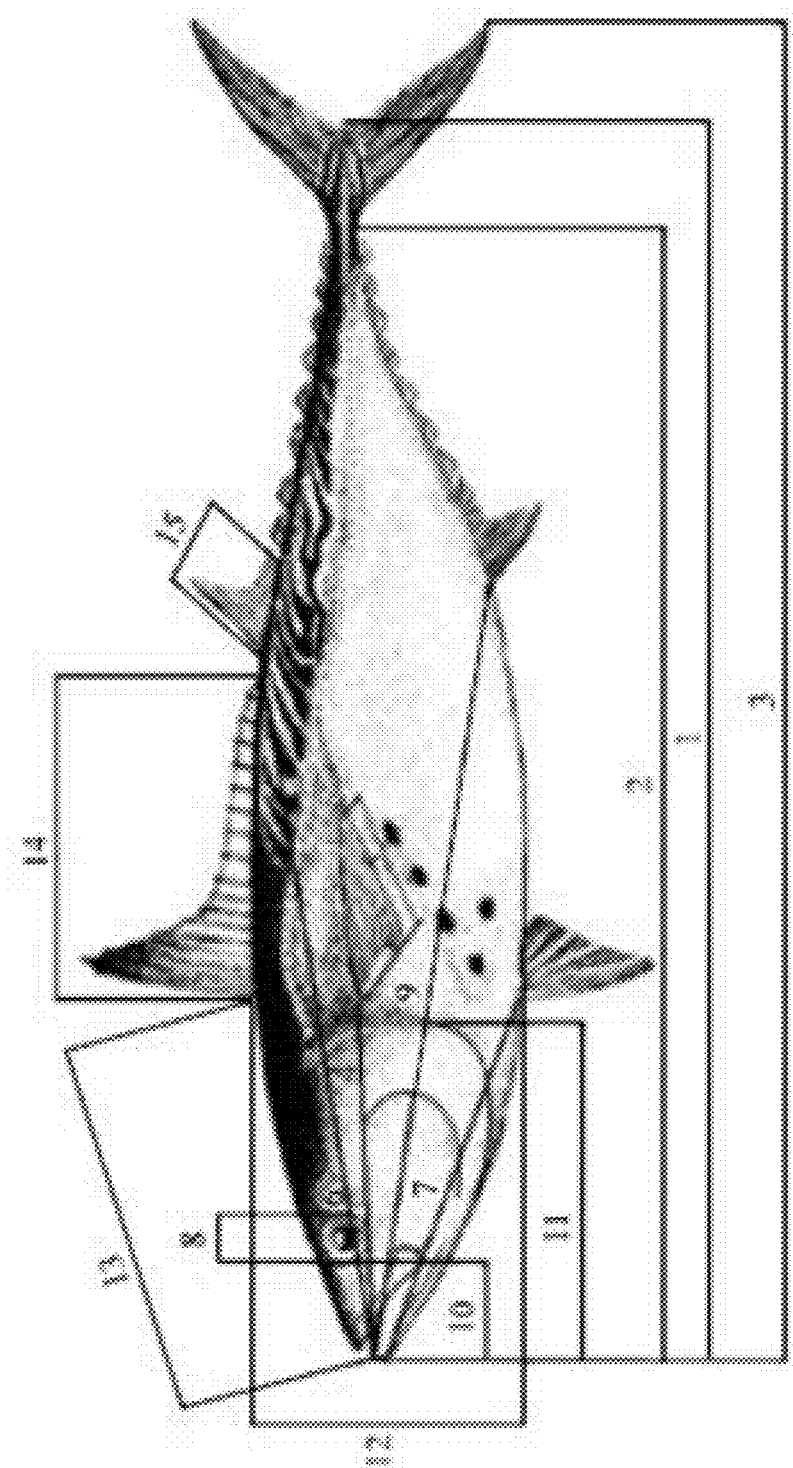
FIG. 4 Morphometric characteristics of the little tuna, *Euthynnus alletteratus*: 1: Fork length (FL); 2: Standard lengths (SL); 3: Total length (TL); 4: Distance of the pectoral fin (DP); 5: Length of pectoral fin (LP); 6: Distance of the second dorsal fin (DD2); 7: Distance of ventral fin (DV); 8: Eye diameter (ED); 9: Distance of anal fin (DA); 10: Snout length (SnL); 11: Head length (HL); 12: Maximum body height (H); 13: Distance of the first dorsal fin (DD1); 14: Length of first dorsal fin base (LD1); 15: Length of second dorsal fin base (LD2).
Figure 5A:
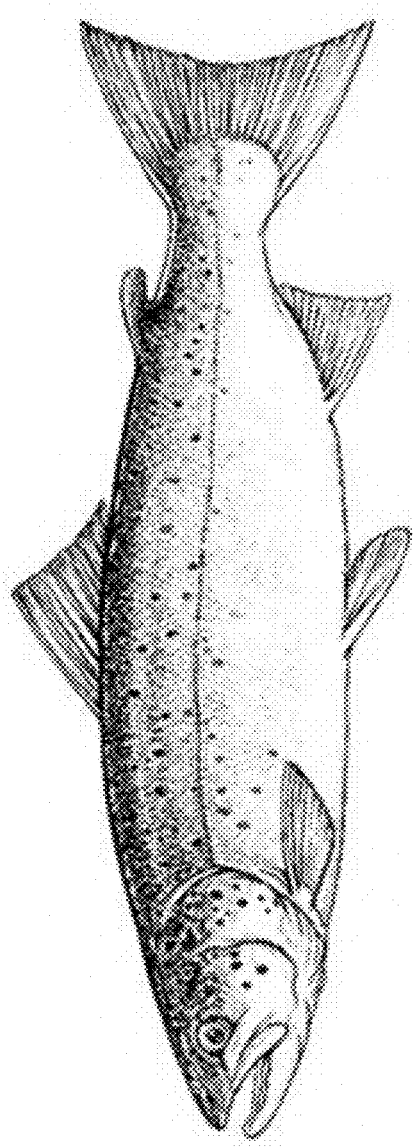
FIG. 5(*a*) is the identification points combining morphometric characteristics of a salmon with (b) to (e) minutiae based skin markings and the distance and location between them.
Figure 5C:
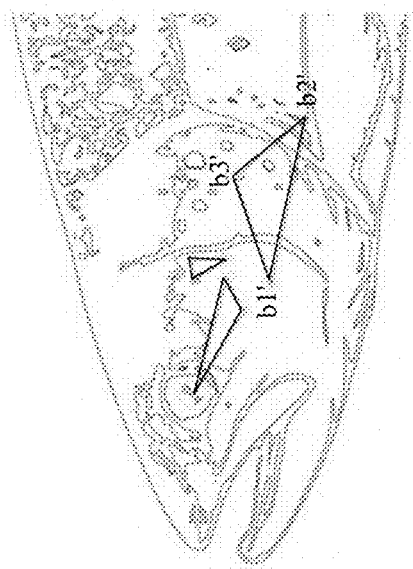
Figure 5B:
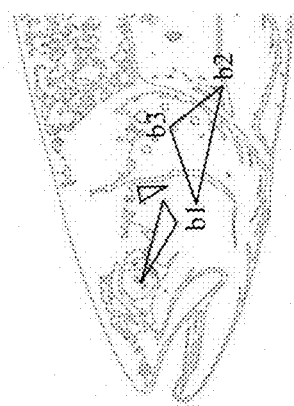
Figure 5D:
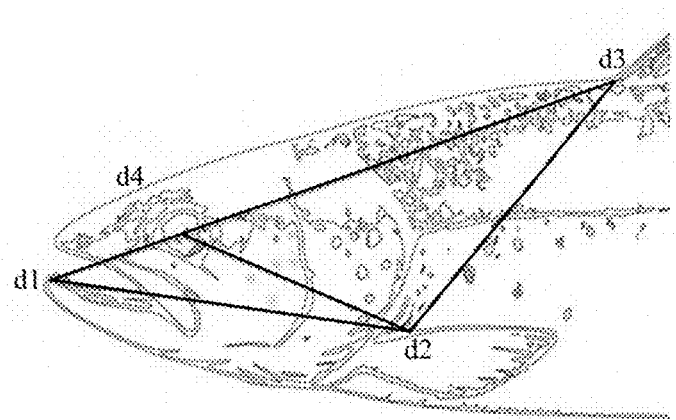
Figure 5E:
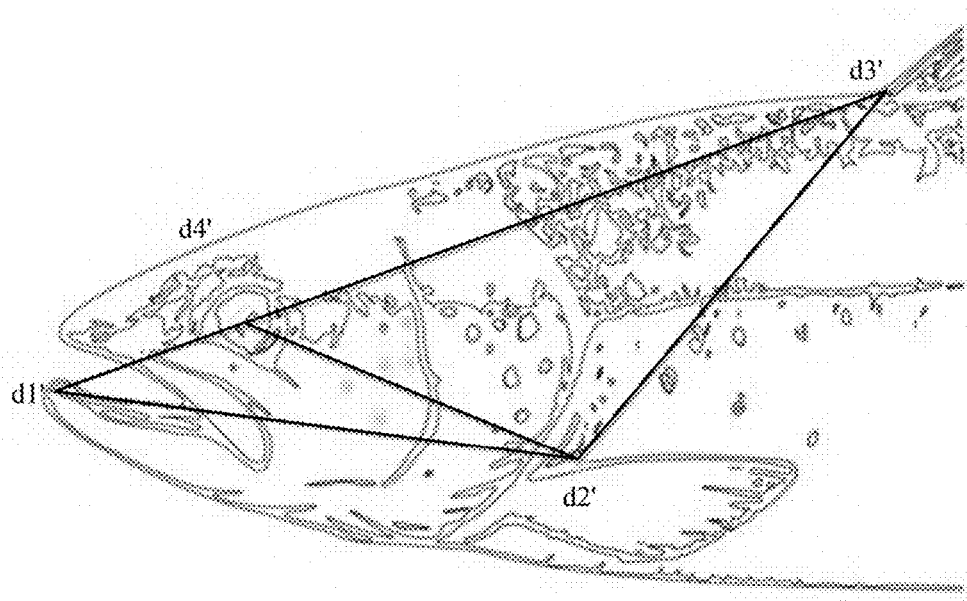

The present invention combines the morphometric characteristics with minutiae based skin markings to identify the individual. FIG. 4 shows the morphometric characteristics of a little tuna, *Euthynnus alletteratus*, as an example. In this example, length of different parts of a fish, such as but not limited to fork length (1), standard lengths (2), total length (3), distance of the pectoral fin (4), length of pectoral fin (5), distance of the second dorsal fin (6), distance of ventral fin (7), eye diameter (8), distance of anal fin (9), snout length (10), head length (11), maximum body height (12), distance of the first dorsal fin (13), length of first dorsal fin base (14), length of second dorsal fin base (15), can be measured and used as morphometric characteristics.

In addition, FIGS. 5(*a*) to 5(*e*) show the identification points combining morphometric characteristics of a salmon with minutiae based skin markings and the distance and location between them. As shown in FIG. 5(*b*), 3 triangular areas (9 markings, such as b1, b2, and b3) are recorded to identify the salmon. The distances between each marking (such as the distance between b1 and b2, b2 and b3, and b1 and b3) are recorded, and the ratio of a distance to another is also recorded. For example, the ratio of the distance between b1 and b2 to the distance between b2 and b3 is 1.81; the ratio of the distance between b2 and b3 to the distance between b1 and b3 is 0.84; the ratio of the distance between b1 and b3 to the distance between b1 and b2 is 0.66. After the salmon grows bigger, as shown in FIG. 5(*c*), the 3 triangular areas (9 markings, such as b1', b2', and b3') are recorded again, and the ratio of the distance between b1' and b2' to the distance between b2' and b3', the ratio of the distance between b2' and b3' to the distance between b1' and b3', and the ratio of the distance between b1' and b3' to the distance between b1' and b2' are calculated. If the ratios of each distance between two markings match a previous record (within a 5% error margin), the fish is identified as the same one. In addition to minutiae based skin markings, markings at certain area can also be used to identify a fish. For example, as shown in FIGS. 5(*d*) and 5(*e*), the end point of lower jaw (d1, d1'), the front point of pectoral fin (d2, d2'), the front point of dorsal fin (d3, d3'), and the central point of an eye (d4, d4') can also be used to identify a fish. By using the morphometric characteristics with minutiae based skin markings, an individual of fish in a pool can be identified.

Characteristics Evaluation

When evaluation of the characteristics is done, there are a lot of factors that will influence the process and results. The algorithms used in this invention need to account all factors that could change or disturb the results within a score.

A classical formula used for calculating fish volume by length/weight relations is (M=aL^b), where M represents mass, a is a constant (depending on specie; cross point) L represents length and b is 3 (cubic).

Further research shows that established formulas does not fit as well as expected when the fish grows bigger. There are indications that also farmed fish becomes relatively heavier with increased length (b>3). Therefore, there are suggestions of using M=bL^2*H—where H is the height of the fish or said highest point is (b=3) or (b≈3). Based on this knowledge, the length and the height of the fish are measured by, for example but not limited to a laser device, to get accurate volume calculations.

A lot of factors have to be encountered. Some of the factors are listed: altitude, temperature, humidity, salinity, illumination, pressure, noise, cuts, scratches, bites, contamination on the sensor, translation directions: up, down, left, right, rotation: roll and yaw. The algorithms chosen to be used evaluate the findings and present the result with a high precision rate.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A computer implemented method for non-invasive biometrical identification of animals, comprising:
   receiving characteristic data of an individual from at least one biometric sensor;
   processing the characteristic data to form biometric data identifying minutiae based skin markings of the individual and biometric data identifying physical characteristics of the individual;
   evaluating the biometric data identifying minutiae based skin markings of the individual and biometric data identifying physical characteristics of the individual to form biometric characteristic data of the individual;
   comparing the biometric characteristic findings of the individual to characteristic data of predetermined registered individuals;
   determining whether the individual is registered;
   giving the individual a unique identification if the individual is not registered; and
   registering the unique identification in a data storage.

2. The computer implemented method of claim 1, further comprising:
   linking the unique identification of the individual to a behavior data collecting system from at least one collecting behavior sensor.

3. The computer implemented method of claim 1, wherein the animals are fish, and the physical characteristics of the individual comprise at least one of body shape, eye, snout, mouth, gilds and fin location.

4. The computer implemented method of claim 1, wherein the animals are birds, the identifying minutiae based skin markings of the individual comprise minutiae based feather markings, and the physical characteristics of the individual comprise at least one of body shape, eye, beacon, wing and leg location.

5. The computer implemented method of claim 1, wherein the animals are pigs, and the physical characteristics of the individual comprise at least one of body shape, eye, snout, mouth, ear, leg and tail location.

6. The computer implemented method of claim 1, further comprising at least one of the following steps:
   processing and discarding images that are not in focus, have visual defects, artifacts, or that are not suitable for further processing;
   processing and analyzing by looking at numbers of individuals within an specific area or volume;
   processing and analyzing by looking for un-normal behavior or sick individuals;
   processing and analyzing by looking for growth rates or volume of individuals increase or decrease;
   processing and analyzing animal health;
   processing and analyzing pandemic control;
   processing and analyzing animal health and using the processed and analyzed data for pandemic control; and
   processing and re-rendering the characteristic data to be able to manually view the data, connected to a unique identification of an individual, and for a person to inspect findings as an image or film.

7. A system for non-invasive biometrical identification of animals, comprising:
   at least one biometric sensor, wherein the at least one biometric sensor captures characteristic data of an individual;
   a characteristic data processing engine, wherein the characteristic data processing engine processes the characteristic data of the individual to form biometric data identifying minutiae based skin markings of the individual and biometric data identifying physical characteristics of the individual;
   a biometric data evaluating engine, wherein the biometric data evaluating engine evaluates the biometric data identifying minutiae based skin markings of the individual and biometric data identifying physical characteristics of the individual to form biometric characteristic data of the individual; and
   a biometric characteristic data comparing engine, wherein the biometric characteristic data comparing engine compares the biometric characteristic data of the individual to characteristic data of predetermined registered individuals, determines whether the individual is registered, gives the individual a unique identification if the individual is not registered, and registers the unique identification in a data storage.

8. The system of claim 7, wherein the at least one biometric sensor comprises at least one of gyro stabilized 2D cameras and gyro stabilized 3D cameras.

9. The system of claim 8, wherein the at least one biometric sensor further comprises a laser device on the at least one of gyro stabilized 2D cameras and gyro stabilized 3D cameras to lock on to a target.

10. The system of claim 7, wherein the at least one biometric sensor comprises at least one camera equipped with an autofocusing apparatus that allows sharp pictures to be taken at various focusing lengths.

11. The system of claim 7, wherein the at least one biometric sensor comprises at least one camera equipped with a fixed focus lens that may capture blurry images for objects that does not fall within the fixed focus distance.

12. The system of claim 7, wherein the characteristic data processing engine comprises algorithms to discard images that are not in focus.

13. The system of claim 7, further comprising:
- a behavior data comparing engine, wherein the physiological characteristic data comparing engine compares physiological characteristic data with a predetermined range of acceptable values for the physiological characteristic data;
- at least one parameter characteristic sensor, wherein the at least one parameter characteristic sensor captures a parameter characteristic of a condition; and
- a parameter characteristic processing engine, wherein the parameter characteristic processing engine receives the parameter characteristic of a condition with a predetermined range of acceptable values and transmits a signal if the individual is registered, if the physiological characteristic data is within the predetermined range, and if the parameter characteristic of the condition to be within the range of acceptable values for the parameter.

14. The system of claim 7, further comprising a data processing and analyzing engine, wherein the data processing and analyzing engine processes and analyzes at least one of numbers of individuals within an specific area or volume, un-normal behavior or sick individuals, growth rates or volume of individuals increase or decrease, animal health, and pandemic control, or processes and re-renders the characteristic data to be able to manually view the data, connected to a unique identification of an individual, and for a person to inspect findings as an image or film.

15. A computer program product for non-invasive biometrical identification of animals, comprising:
- a non-transitory computer recordable-type medium;
- first program instructions for receiving characteristic data of an individual from at least one biometric sensor;
- second program instructions for processing the characteristic data to form biometric data identifying minutiae based skin markings of the individual and biometric data identifying physical characteristics of the individual;
- third program instructions for evaluating the biometric data identifying minutiae based skin markings of the individual and biometric data identifying physical characteristics of the individual to form biometric characteristic data of the individual;
- fourth program instructions for comparing the biometric characteristic data of the individual to characteristic data of predetermined registered individuals, determining whether the individual is registered, giving the individual a unique identification if the individual is not registered, and registering the unique identification in a data storage; and
- wherein the first program instructions, the second program instructions, the third program instructions, and the fourth program instructions are stored on the non-transitory computer recordable-type medium.

16. The computer program product of claim 15, further comprising:
- fifth program instructions for linking the unique identification of the individual to receive behavior data of the individual from the at least one biometric sensor;
- sixth program instructions for comparing behavior data with a predetermined range of acceptable values for the physiological characteristic data;
- seventh program instructions for receiving a parameter characteristic of a condition with a predetermined range of acceptable values for the parameter transmitting a signal if the individual is registered, if the physiological characteristic data is within the predetermined range, and if the parameter characteristic of the condition to be within the range of acceptable values for the parameter; and
- wherein the fifth program instructions, the sixth program instructions, and the seventh program instructions are stored on the non-transitory computer recordable-type medium.

17. The computer program product of claim 15, further comprising eighth program instructions for processing and analyzing at least one of: numbers of individuals within an specific area or volume, un-normal behavior or sick individuals, growth rates or volume of individuals increase or decrease, animal health, and pandemic control, or processing and re-rendering the characteristic data to be able to manually view the data, connected to a unique identification of an individual, and for a person to inspect findings as an image or film, wherein the eighth program instructions are stored on the non-transitory computer recordable-type medium.

* * * * *